United States Patent [19]
Kuo et al.

[11] Patent Number: 4,716,117
[45] Date of Patent: Dec. 29, 1987

[54] MONOCLONAL ANTIBODIES TO FACTOR VIIIC

[75] Inventors: George Kuo; Frank R. Masiarz, both of San Francisco; Martha Truett, Oakland; Pablo Valenzuela, San Francisco, all of Calif.; Mirella E. Rasmussen, Copenhagen, Denmark; Jennifer Favaloro, Victoria, Australia

[73] Assignees: Chiron Corporation, Emeryville, Calif.; Nordisk Gentofte, Gentofte, Denmark

[21] Appl. No.: 689,274

[22] Filed: Jan. 7, 1985

Related U.S. Application Data

[63] Continuation-in-part of Ser. No. 664,919, Oct. 26, 1984, abandoned, which is a continuation-in-part of Ser. No. 570,062, Jan. 12, 1984.

[51] Int. Cl.[4] .................. A61K 39/395; G01N 33/597

[52] U.S. Cl. ............................ 435/240.27; 435/172.2; 435/68; 436/548; 935/89; 935/95; 935/102; 935/103; 935/104; 935/105; 935/106; 935/108; 935/110; 424/85

[58] Field of Search .................... 436/548; 935/89, 95, 935/102-106, 108, 110; 435/240, 68, 172.2; 424/85

[56] References Cited

U.S. PATENT DOCUMENTS 4,361,509 11/1982 Zimmerman et al. .......... 260/112 B
4,649,132 3/1987 Zimmerman et al. .
4,657,894 4/1987 Zimmerman et al. .

FOREIGN PATENT DOCUMENTS 53519 3/1984 Denmark .......................... 260/12 B
123945 11/1984 European Pat. Off. .
1157556 10/1985 European Pat. Off. .
160457 11/1985 European Pat. Off. .
182372 5/1986 European Pat. Off. .
8501961 10/1984 PCT Int'l Appl. .
8404541 11/1984 PCT Int'l Appl. .

OTHER PUBLICATIONS

Fulcher & Zimmerman, Proc. Natl. Acad. Sci USA (1982) 79: 1648-1652.
Tuddenham et al., (1979) J. of Lab. Clinical Medicine, 93: 40-53.
Austen, (1979), British J. Hematology, 43: 669-674.
Weinstein et al., (1981), Proc. Natl. Acad. Sci USA, 78: 5137-5141.
Kuo et al., Abstracts for IX International Congress of Thrombosis Hemostasis, (Stockholm, Jul. 1983).
Hybritech Data Sheet (Catalogue #0432).
Fulcher et al., (1983) Blood 61: 807.
Fass et al., (1982) Blood 59: 594.
Kurachi et al., (1982), Proc. Natl. Acad. Sci. USA 79: 6461-6464.
Maniatis et al., *Molecular Cloning: A Laboratory Manual,* pp. 224-228, (1982).
Bloom, (1983), Nature 303: 474-475.
Muller et al., (1981), Blood 58: 1000-1006.
Maddox, (1983), Nature 306: 528.
Rotblat et al., (1984), Biological Abstracts 77: 4443, (Abstract No. 40713).
Rotblat et al., (1983), J. Lab. Clin. & Med. 101: 736-746.
Wood et al., (1984), Nature 312: 330-337.
Toole et al., (1984), Nature 312: 342-347.

*Primary Examiner*—Christine M. Nucker
*Attorney, Agent, or Firm*—Ciotti & Murashige, Irell & Manella

[57] ABSTRACT

Hybridomas producing monoclonal antibodies specific for polypeptide fragments derived from human Factor VIIIC are provided. Class I hybridomas produce monoclonal antibodies reactive with a 80/77 kd doublet fragment or with both the 80/77 kd doublet and a 240 kd polypeptide. Class III hybridomas produce monoclonal antibodies reactive with the 240 kd polypeptide as well as a 92.5 kd fragment and its precursors. Class III antibodies show additional reactivity with a 40 kd thrombin digestion product. The monoclonal antibodies are useful for the separation of Factor VIIIC and its constituent polypeptides, as well as for the immunoassay of Factor VIIIC in biological samples.

4 Claims, No Drawings

MONOCLONAL ANTIBODIES TO FACTOR VIIIC

This application is a continuation-in-part of application Ser. No. 664,919, filed Oct. 26, 1984, now abandoned which is a continuation-in-part of application Ser. No. 570,062 filed Jan. 12, 1984.

BACKGROUND OF THE INVENTION

1. Field of the Invention

Factor VIIIC is a plasma protein that participates in the intrinsic pathway of blood coagulation. It is absent or defective in individuals with the hereditary X chromosome-linked recessive bleeding disorder hemophilia A. Great difficulty has been encountered in isolating Factor VIIIC due to its extremely low concentration in plasma and the fact that it appears to be an intermediate or final degradation product of a larger protein precursor. Efforts to isolate Factor VIIIC have led to complex mixtures of various polypeptides having significant heterogeneity and varying molecular weights.

It would be of great interest therefore to prepare monoclonal antibodies which are capable of selectively reacting with individual polypeptides or groups of polypeptides which are derived from Factor VIIIC.

2. Description of the Prior Art

U.S. Pat. No. 4,361,509 and references cited therein describe purification of Factor VIIIC. See also Fulcher and Zimmerman, *Proc. Natl. Acad. Sci. USA* (1982) 79:1648-1652. Tuddenham et al., *J. of Lab. Clinical Medicine* (1979) 93:40-53 describes purification of Factor VIIIC using polyclonal antibodies. Austen, *British J. Hematology* (1979) 43:669-674 describes the use of aminohexyl-Sepharose for Factor VIIIC purification. Weinstein et al., *Proc. Natl. Acad. Sci. USA* (1981) 78:5137-5141 describes a study of the effect of thrombin on Factor VIIIC. See also Kuo et al., Abstracts for IX International Congress of Thrombosis and Hemostasis, (Stockholm; July, 1983).

Hybritech Data Sheet (Hybritech, Inc., 11085 Torreyana Road, San Diego, Calif. 92121) describes a monoclonal antibody (Catalog #0432) which is specific for human Factor VIIIC. Danish patent application No. 53519 corresponding to U.S. patent applications Ser. Nos. 481,103 filing date 3-31-83 and 556,508 filing date 11-30-83 describes the preparation of monoclonal antibodies to human factor VIIIC and polypeptide fragments thereof. Certain of the monoclonal antibodies described in the Danish patent application are also described by Zimmerman et al. (1983) Blood 61:807. Fass et al. (1982) Blood 59:594, report that active human Factor VIIIC may be eluted from monoclonal antibodies by ethylene glycol (50%).

SUMMARY OF THE INVENTION

Particular hybridoma cell lines producing monoclonal antibodies reactive with human Factor VIIIC are provided. Monoclonal antibodies produced by cell lines 42, 47 and 56 are reactive with a 80/77 kd doublet obtained by electrophoresis of Factor VIIIC material under denaturing conditions. Monoclonal antibodies produced by cell lines 1B9, 2B6 and 2F6 react with the 80/77 kd doublet and with a 240 kd fragment. Monoclonal antibodies produced by cell lines 4E5 and 5B1 react with the 240 kd fragment, the 92.5 kd fragment and its precursors, as well as a 40 kd thrombin digestion product of Factor VIIIC material. Of the above, only antibodies produced by 56 cell lines displayed coagulation inhibition.

DESCRIPTION OF THE SPECIFIC EMBODIMENTS

Hybridomas producing monoclonal antibodies reactive with different polypeptide fragments of human Factor VIIIC are provided. Class I hybridomas produce monoclonal antibodies reactive with a 80/77 kd doublet fragment of Factor VIIIC or with both a 240 kd fragment and a 80/77 kd doublet. Class III hybridomas produce monoclonal antibodies reactive with the same 240 kd fragment as well as a 92.5 kd fragment and precursors thereof. Class III antibodies show an additional reactivity with a 40 kd thrombin digestion product of Factor VIIIC material.

Human Factor VIIIC is a complex protein which can be isolated in substantially pure form and exhibits an apparent molecular weight of about 460 kd. Upon electrophoresis under denaturing conditions, a large number of fragments of varying molecular weights result: 240, 160, 140, 115, 92.5, 80 and 77 kd, the latter two being found to migrate as a doublet. Analysis of the fragments by chemical and protease cleavage including thrombin, employing the monoclonal antibodies of the present invention to follow immunogenic relationships and cleavage patterns to follow structural relationships, demonstrates that the 92.5 kd polypeptide is related to the 240, 160, 140 and 115 polypeptides while the 77/80 doublet appears to have common antigenic characteristics with only the 240 kd polypeptide. It is further found that the 77/80 kd doublet is converted by thrombin to a 67/70 kd doublet, while the 92.5 kd polypeptide present in purified Factor VIIIC material treated with thrombin is cleaved by thrombin, directly or indirectly, into two polypeptides of about 40 and 52.5 kd.

The monoclonal antibodies of the present invention are useful for a variety of purposes. For example, the antibodies may be used to isolate the entire Factor VIIIC complex from plasma, as well as isolating the various polypeptide fragments of Factor VIIIC from a purified source. In addition, the antibodies may be used for detecting the presence of Factor VIIIC and related polypeptides in plasma by a variety of immunoassay techniques. Suitable immunoassay techniques are well known and amply described in the scientific and patent literature.

The monoclonal antibodies of the present invention may also be used to facilitate preparation of additional hybridomas producing monoclonal antibodies having substantially identical reactivity, but often differing in other characteristics, such as isotype, binding affinity, and the like. This can be achieved by using the monoclonal antibody to enrich these polypeptides carrying determinant sites recognized by the antibody in a source Factor VIIIC. Conveniently, an affinity column may be prepared using the desired antibody. By then applying the Factor VIIIC to the column in an appropriate buffer, polypeptides recognized by the antibody will be bound. After washing the column to assure removal of non-specifically bound proteins, the polypeptide of interest may be released from the column by adjusting the pH, employing urea, or by utilizing other mildly denaturing conditions. The antigen may then be isolated and used to hyperimmunize an appropriate host, and hybridomas produced by the now classical teachings of Kohler and Milstein (1975) Nature 256:495, or more recent adaptations thereof. Details of suitable immunization, immortalization, and screening procedures are set forth below. Following such procedures, a variety of antibodies having substantially identical reactivities, but differing in class, binding constant, host, and the like, can be obtained.

In general, hybridomas may be produced by first hyperimmunizing a mouse or other small mammal with the Factor VIII polypeptide of interest. Specific methods of immunization are well known and are amply described in the literature. The Factor VIII polypeptide is injected with or without adjuvants into the mammal followed by from 2 to 6 subsequent booster injections over a relatively short period of time. The animals are then killed, usually several days after the final injection, the spleens removed, and the spleen cells immortalized.

The manner of immortalization is not critical. Presently, the most common way is fusion with a myeloma cell fusion partner, which method is exemplified here. Other techniques include EBV transformation, transformation with bare DNA, e.g., oncogenes, retroviruses, etc., or any other method which provides for stable maintenance of the cell line and production of monoclonal antibodies.

When employing fusion with fusion partner, the manner of fusion is not critical and various techniques may be employed. Conveniently, the spleen cells and myeloma cells are combined in the presence of polyethylene glycol, a suitable growth medium, and other additives for a few minutes. At the end of the fusion, the non-ionic detergent is removed by washing the cells.

The fused cells are then promptly dispensed into small culture wells, usually in a microtiter plate, at relatively low density for screening. The growth medium in the culture wells is selected to support growth of the hybrid cells while being lethal to the myeloma cells. Conveniently, the myeloma cell line has been mutated to be sensitive to particular agents, typically being HAT sensitive.

After sufficient time, usually from one to two weeks, colonies of hybrids are observed and plates containing positive wells are identified. The plates and wells having only one colony per well are selected, and the supernatants from these wells are tested for binding activity against the particular polypeptide fragment(s) of Factor VIIIC. Other characteristics of the hybridoma cell line and monoclonal antibodies, such as growth characteristics of the hybridoma, binding affinity of the monoclonal antibodies, antibody class, cross-reactivity of the antibodies, and the like, can then be determined. Those hybridomas which produce antibodies having the desired specificity as well as other desirable characteristics can then be maintained as viable cultures and/or frozen storage.

The following examples are offered by way of illustration, not by way of limitation.

EXPERIMENTAL

1. Purification of Factor VIIIC

Human Factor VIIIC was isolated from commercial cryoprecipitate preparations by (a) immunosorbent chromatography using a polyclonal anti VIIIR-Sepharose column by a method first described by E. G. D. Tuddenham, N. C. Trabold, J. A. Collins, and L. W. Hoyer, *J. of Lab. Clinical Medicine* (1979) 93:40; and (b) a chromatographic separation on aminohexyl-substituted agarose as was originally described by D. E. G. Austen, *British J. of Hematology* (1979) 43:669. Details of the procedures are described below.

Goat anti-human Factor VIII Related Antigen (VIIIR) serum obtained from *Atlantic Antibody* (cat. no. 040-01), was treated with either a standard 0–50% ammonium sulfate cut followed by DEAE cellulose column chromatography, or a similar 0–33% cut without subsequent chromatography. These materials were then conjugated to CNBr-activated Sepharose CL2B or 4B, respectively, (Pharmacia, 17-0140-01 or 17-0430-01) and poured as a column (anti VIIIR-Sepharose column).

"HEMOFIL", a stable, dried preparation of antihemophilic factor (Factor VIII, AHF, AHG) in concentrated form prepared from fresh, normal human plasma, representing about a 40-fold enrichment for Factor VIIIC, was dissolved in the following buffer: 0.02M imidazole, 0.15M NaCl, 0.1M lysine-HCl, 0.02% $NaN_3$, pH 7.4.

After being dissolved, the Hemofil was applied to the above-described anti VIIIR-Sepharose column. Non-specifically bound protein was eluted with the above buffer modified to 0.5M NaCl. Next, Factor VIIIC was eluted with the above buffer containing 0.35M $CaCl_2$, with the addition of 10% glycerol which stabilizes the Factor VIIIC activity. Active fractions from the immunosorbent column were pooled and dialyzed against buffer (0.02M imidazole, 0.15M NaCl, 0.1M lysine-HCl, 0.025M $CaCl_2$, 0.02% $NaN_3$, 10% glycerol, pH 7.4). An aliquot of the dialyzed fractions, which contained 1,100 units of Factor VIIIC, was applied to an aminohexyl-Sepharose 4B column ($1\times6$ cm) equilibrated with dialysis buffer described above. Factor VIIIC activity was eluted with the same buffer containing either 0.35M $CaCl_2$ or 2M NaCl. The activity was found to be in a volume of 2 ml with 500 units of Factor VIIIC per ml. Subsequent experiments carried out in the same manner provided a recovery of 25% off the anti VIIIR column and a recovery of approximately 90% off the aminohexyl column. Alternatively, pooled, dialysed material eluted from the immunosorbent column is first applied to a dextran sulfate agarose (Pharmacia) column ($1.5\times6$ cm) equilibrated with the dialysis buffer above and eluted with the same buffer. Several minor contaminants, e.g., fibrinogen, fibronectin, IgG, are retained on the column while Factor VIIIC emerges in the flow-through which is collected and loaded on the aminohexyl-Sepharose column as before.

Both biological, i.e., clotting, and antigenic (CAg) activity were shown to be present in the purified Factor VIIIC, as demonstrated by the subsequent assays indicating a 5,000-fold purification over the 40-fold concentration in Hemofil. Using a standard commercially available three component kit from General Diagnostics, (APTT, Factor VIII deficient plasma, Verify Normal Citrate) a coagulation assay was carried out and indicated high levels of Factor VIIIC biological activity.

2. Preparation of Monoclonal Antibodies

Balb/c mice were immunized with purified human Factor VIIIC, as described above. Spleen cells ($10^8$) were fused with $10^7$ NSO or $10^7$ NSI mouse myeloma cells (according to Kohler and Milstein (1975) Nature 256:495). The products of each fusion were plated onto two 96 well microtiter plates. A spleen cell feeder layer was used at $10^4$ cells/well. Colonies were visible microscopically from the fifth day, and the supernatants were assayed every few days for presence of antibodies against Factor VIIIC. An enzyme linked immunoadsorbent assay (ELISA) was used employing the following layers in an immunoassay plate (Nunc F2):

1st layer: Monospecific anti-mouse Ig
2nd layer: Hybridoma cell supernatant
3rd layer: Cryo-precipitate containing human Factor VIIIC
4th layer: Peroxidase labelled IgG from a hemophilic inhibitor patient.

Four positive cell lines were identified, purified by subcloning and grown in liter scale cultures in the laboratory. Three of the positive cell lines, designated 42, 47 and 56, were derived from fusions with the NSO myeloma cell line. The fourth positive cell line was derived from fusion with the NS-1 myeloma cell line and designated 1-28.

Other fusions were performed in the manner just described except that the fusion partner was cell line P3X63Ag8,653 (Kearney et al. (1979) J. Immunol. 123:1548-1550). ELISA screening was performed with the following layers:

1st layer: Purified Factor VIIIC
2nd layer: Hybridoma cell supernatant
3rd layer: Horseradish peroxidase (HRP)-labelled goat anti-mouse IgG
4th layer: HRP-substrate Five positive cell lines were identified, subcloned, grown in liter scale cultures and characterized as described in Section 4. The cell lines were designated as 1B9, 2B6, 2F9, 4E5 and 5B1.

3. Amplification of Positive Hybridomas

In order to be certain that each hybridoma producing anti-Factor VIII antibodies was free from cells producing other immunoglobulins and cells not producing immunoglobulins, purification by subcloning was performed. Dilutions of hybridoma cells 42, 47, 56 and 28 were seeded in microtiter plates, such that each well theoretically contained a single cell. When necessary because of low cloning efficiency, initial seeding was at two cells per well followed by a second seeding at one cell per well. After 7 to 14 days, supernatants from each colony of presumptively identical cells derived from each hybridoma cell line were screened to identify the anti-Factor VIII producing colonies. The positive subclones were then expanded to macroculture.

Multiple aliquots of each cell line were frozen in liquid nitrogen as soon as purification was complete. This provided amplification of the cultures from the original single microwell ($10^2$ cells in 0.2 ml) to about $10^8$ cells, which corresponded to about 100 ml of medium. The cells were very sensitive during this stage of growth and improper handling could result in death of the culture. Although individual characteristics of each cell line meant that identical procedures could not be used for all four lines, the following steps were generally employed to keep the cultures alive and growing:

1. Micro wells were approximately ¼ confluent before transfer to macroculture.
2. Pre-conditioned medium was used for the first two weeks of subculture.
3. Transfer from macro to flask culture was delayed until at least 4 ml of macroculture was grown to half-confluence.
4. Dilution of the flask culture was limited to less than 1:2 for the first few passages.

4. Characterization of Monoclonal Antibodies

To identify the immunoglobulin class of the monoclonal anti-Factor VIIIC antibodies, an immunoassay for mouse IgG was carried out in which the coating antibodies were specific for immunoglobulin-subclasses. Microplates precoated with anti-isotype antibodies were obtained from Hagedorn Research Lab. The antibodies produced by hybridoma cell lines 42, 47 and 56 were found to be IgG 1, while those produced by cell line 5B1 were found to be IgM.

Two classes of monoclonal antibodies were identified according to their reactivity with Factor VIIIC polypeptides using the following procedure. Hybridoma culture supernatants were incubated for 12 hours at room temperature with polystyrene beads (⅛" diameter, Precision Plastic Ball Co., Chicago) coated with affinity-purified goat anti-mouse immunoglobulin (IgG). The polystyrene beads were washed with phosphate-buffered saline and reacted with purified Factor VIIIC labelled with $I^{125}$ using the chloramine T method. The labelled proteins bound on the beads were solubilized in SDS sample buffer for gel electrophoresis and were separated on an 7.5% acrylamide gel (Laemmli (1970) Nature 227: 680–685). The gel was fixed, dried and exposed to Kodak X-Omat film with an intensifying screen for 20 hours or longer at −80° C. The results obtained with this procedure allowed classification of the monoclonal antibodies as follows:

Class I: react with the 80/77 kd doublet or with the 80/77 kd doublet and a 240 kd protein. These antibodies also react with a 70/67 kd doublet when thrombin-digested Factor VIII is used in the assay, indicating that the 70/67 kd doublet produced by thrombin digestion, is derived from the 80/77 kd doublet.

Class III: react with 240, 140, 115, 92.5 kd proteins as well as with a 40 kd peptide produced by thrombin digestion of purified Factor VIIIC material.

Table 1 indicates the Class corresponding to each of the monoclonal antibodies produced by the different hybridoma cell lines.

TABLE 1

Classification of monoclonal antibodies

| | Cell Lines |
|---|---|
| Class I: | IB9; 2B6; 2F9; 42; 47; 56; I-28 |
| Class III: | 4E5; 5B1 |

The antibodies were screened for Factor VIIIC coagulation inhibition activity using the conventional Bethesda assay (C. Kasper (1975) Thrombos. Diathes. Haemorrh. 34: 869–782). Of the above antibodies, only those produced by cell line 56 displayed coagulation inhibition activity.

The following experiments were performed to study the association between the 92.5 kg protein and the 80/77 kd doublet, as well as to investigate the role of calcium in the association. The following ELISA assay were performed in the presence of 10 mM $CaCl_2$ or in the presence of the same concentration of $CaCl_2$, 10 mM EGTA, and 10 mM EDTA.

1st layer: Monospecific anti(mouse IgG)
2nd layer: Class III monoclonal antibody (anti-92.5 kd) or Class I monoclonal antibody (anti-80/77 kd)
3rd layer: Purified Factor VIIIC material
4th layer: HRP-human inhibitor antibody to 77/80 kd The results are shown in Table 2. As Table 2 shows, a strong HRP reaction is obtained when only calcium is present in the assay, indicating that the 4th layer (HRP-human inhibitor antibody to 77/80 kd) is binding to the complex associated to the Class III monoclonal antibody. When EGTA and EDTA are added to the assay, HRP activity bound in the assay corresponds only to non-specific binding. These results demonstrate that the 92.5 kd protein is bound to the 80/77 kd doublet through calcium bridges.

TABLE 2

Role of calcium in the association of 80/77 kd doublet to 92.5 kd protein

| | Antibody specificity (2nd layer) | | | |
|---|---|---|---|---|
| | $CaCl_2$ | | CaCl + EGTA + EDTA | |
| | $A_{495}$ sample | $A_{495}$ sample $A_{495}$NSB* | $A_{495}$ sample | $A_{495}$ sample $A_{495}$NSB* |
| Non-specific binding* | 0.229 | 1 | 0.068 | 1 |
| Medium only** | 0.248 | 1.08 | 0.67 | 0.99 |
| Class III (5B1) (92.5 kd) | 0.939 | 4.10 | 0.071 | 1.04 |
| Class I (47) (80/77 kd) | 1.81 | 7.9 | 0.523 | 7.69 |

*Non-specific binding (NSB) was measured by the ELISA assay deleting the FVIIIC material.

**Medium only was added instead of the monoclonal antibody (2nd layer) in the ELISA assay.

Additional assays were performed to characterize the monoclonal antibodies in terms of the epitopes they recognized. Competition assays were performed by reacting Factor VIIIC immobilized on microtiter wells with $^{125}$I-42 IgG or $^{125}$I-47 IgG and unlabelled 42, 47, 56 and I-28 at various dilutions. The results showed that 47 and 42 monoclonal antibodies react with different epitopes. They also showed that it is likely that 56 monoclonal antibodies react with an epitope near the binding site of 42 monoclonal antibodies and induce a conformation change in VIIIC that enhances the affinity for 42 antibodies.

Monoclonal antibodies capable of distinguishing between various of the constituent polypeptides of Factor VIIIC are provided. Class I antibodies react with a 80/77 kd doublet or with both a 240 kd fragment and a 80/77 kd doublet. Class III monoclonal antibodies react with the 240 kd polypeptide, as well as a 92.5 kd polypeptide and its precursors. Class III antibodies show an additional reactivity with a 40 kd thrombin digestion product of the Factor VIIIC material.

Cell lines for 4E5, 5B1, and 2B6 were deposited with the American Type Culture Collection, 12301 Park Lawn Drive, Rockville, MD 20852, USA, and have been assigned accession numbers HB 8688, HB 8689, and HB 8690, respectively. Cell lines 42, 47, 56, and I-28 were deposited with the National Collection of Animal Cell Cultures, Porton Down, Salisbury, United Kingdom, and have been assigned accession numbers 84 12 21 03, 84 12 21 02, 84 12 21 04, and 84 12 21 01, respectively.

Although the foregoing invention has been described in some detail for purposes of clarity of understanding, it will become obvious that certain changes and modification may be practiced within the scope of the appended claims.

What is claimed is:

1. A hybridoma cell line selected from the group consisting of cell line 42, cell line 47, cell line 56, cell line 1-28, cell line 4E5, cell line 5B1, and, cell line 2B6.

2. Monoclonal antibodies obtained from any of the hybridoma cell lines of claim 1.

3. A hybridoma cell line producing monoclonal antibodies that block the binding of any of the monoclonal antibodies of claim 2 to their epitope in a competition assay.

4. Monoclonal antibodies obtained from any of the hybridoma cell lines of claim 3.

* * * * *